United States Patent
Ichiki et al.

(10) Patent No.: US 9,952,215 B2
(45) Date of Patent: Apr. 24, 2018

(54) EXOSOME ANALYSIS METHOD, EXOSOME ANALYSIS APPARATUS, ANTIBODY-EXOSOME COMPLEX, AND EXOSOME ELECTROPHORESIS CHIP

(71) Applicants: The University of Tokyo, Tokyo (JP); NIKON CORPORATION, Tokyo (JP)

(72) Inventors: Takanori Ichiki, Tokyo (JP); Takanori Akagi, Tokyo (JP); Hirofumi Shiono, Fujisawa (JP)

(73) Assignees: The University of Tokyo, Tokyo (JP); Nikon Corporation, Tokyo (JP)

( * ) Notice: Subject to any disclaimer, the term of this patent is extended or adjusted under 35 U.S.C. 154(b) by 196 days.

(21) Appl. No.: 14/629,028

(22) Filed: Feb. 23, 2015

(65) Prior Publication Data
US 2015/0168400 A1    Jun. 18, 2015

Related U.S. Application Data

(63) Continuation of application No. PCT/JP2013/071967, filed on Aug. 15, 2013.

(30) Foreign Application Priority Data

Aug. 24, 2012 (JP) ................... 2012-185666

(51) Int. Cl.
*G01N 27/447*  (2006.01)
*G01N 33/566*  (2006.01)
(Continued)

(52) U.S. Cl.
CPC ....... *G01N 33/566* (2013.01); *G01N 33/5432* (2013.01); *G01N 33/54346* (2013.01);
(Continued)

(58) Field of Classification Search
CPC ............. G01N 33/566; G01N 33/5432; G01N 33/54346; G01N 33/561; G01N 33/57484;
(Continued)

(56) References Cited

U.S. PATENT DOCUMENTS 5,686,252 A    11/1997 Nishizaki
5,854,082 A *  12/1998 Kubotsu ............ G01N 33/5432
                                                    435/975
(Continued)

FOREIGN PATENT DOCUMENTS

JP         2924815 B2    7/1999
JP      2011-106915    * 11/2009
(Continued)

OTHER PUBLICATIONS

C. Lasser et al., "Isolation and Characterization of RNA-Containing Exosomes", Journal of Visualized Experiments. v. 59, e3037, Jan. 2012, pp. 1-8.
(Continued)

*Primary Examiner* — J. Christopher Ball
(74) *Attorney, Agent, or Firm* — Foley & Lardner LLP (57) ABSTRACT

A method of analyzing an exosome is provided for detecting abnormality in a cell, including: (a) a step of preparing an exosome from a sample; (b) a step of bringing the exosome prepared in the step (a) into contact with a first antibody to a protein which exists on the surface of the exosome as an antigen and forming a first antibody-exosome complex; and (c) a step of measuring a zeta potential of the first antibody-exosome complex.

12 Claims, 4 Drawing Sheets

(51) Int. Cl.
*G01N 33/574* (2006.01)
*G01N 33/543* (2006.01)
*G01N 33/561* (2006.01)

(52) U.S. Cl.
CPC ..... *G01N 33/561* (2013.01); *G01N 33/57484* (2013.01); *G01N 27/44752* (2013.01); *G01N 27/44791* (2013.01); *G01N 2333/70596* (2013.01); *G01N 2550/00* (2013.01)

(58) Field of Classification Search
CPC ....... G01N 27/44791; G01N 27/44752; G01N 2550/00; G01N 2333/70596
See application file for complete search history.

(56) References Cited

U.S. PATENT DOCUMENTS

| | | | |
|---|---|---|---|
| 6,051,124 | A | 4/2000 | Aoki |
| 8,617,806 | B2 | 12/2013 | Fais et al. |
| 2009/0220944 | A1 | 9/2009 | Fais et al. |
| 2010/0255514 | A1 | 10/2010 | Rak et al. |
| 2010/0332183 | A1 | 12/2010 | Nooney et al. |
| 2012/0077963 | A1* | 3/2012 | Hongo ................ C07K 16/065 530/388.1 |

FOREIGN PATENT DOCUMENTS

| | | |
|---|---|---|
| JP | 2010-537158 A | 12/2010 |
| JP | 2011-510309 A | 3/2011 |
| JP | 2011-106915 A | 6/2011 |
| WO | WO 2009/021322 A1 | 2/2009 |
| WO | WO 2009/092386 A2 | 7/2009 |

OTHER PUBLICATIONS

E. Charafe-Jauffret et al., "Gene expression profiling of breast cell lines identifies potential new basal markers", Oncogenomics, 2006, pp. 2273-2284.
International Search Report and Written Opinion with English Translation, 14 pages.
Nishima Wangoo et al. "Zeta potential based colorimetric immunoassay for the direct detection of diabetic marker HbA1c using gold nanoprobes", Chemical Communications-Chemcom, vol. 46, No. 31, Jan. 1, 2010 (Jan. 1, 2010), pp. 5755, XP055247312, GB ISSN: 1359-7345, DOI: 10.1039/c0cc00224k.
Partial Supplementary European Search Report issued in European Application No. 13831760.7 dated Feb. 18, 2016.
Office Action dated Feb. 7, 2017, in JP 2014-531606, with English translation.
Office Action dated Jul. 18, 2017, in JP 2014-531606 with English translation.

* cited by examiner

EXOSOME ANALYSIS METHOD, EXOSOME ANALYSIS APPARATUS, ANTIBODY-EXOSOME COMPLEX, AND EXOSOME ELECTROPHORESIS CHIP

CROSS-REFERENCE TO RELATED APPLICATION

This is a Continuation Application of International Application No. PCT/JP2013/071967, filed Aug. 15, 2013, which claims priority to Japanese Patent Application No. 2012-185666 filed in Japan on Aug. 24, 2012. The contents of the aforementioned applications are incorporated herein by reference.

BACKGROUND

The present invention relates to an exosome analysis method, an exosome analysis apparatus, an antibody-exosome complex, and an exosome electrophoresis chip.

An exosome is a small lipid vesicle with a diameter of 30 nm to 100 nm, and is secreted as a fusion between an endosome and a cell membrane in body fluids such as blood, urine, and saliva from various cells such as tumor cells, dendritic cells, T cells, and B cells.

In some cases, an abnormal cell, such as a cancer cell, expresses unique protein in a cell membrane. Protein derived from a cell of a secretory source is expressed in a membrane surface of an exosome. For this reason, there is a possibility of determining the characteristics of the cell of the secretory source by analyzing protein on the membrane surface of the exosome in a body fluid, and to establish examination techniques through which it is possible to examine abnormality in a living body without performing a biopsy. The term biopsy refers to a clinical procedure to diagnose disease by collecting tissue from a lesion area and observing it using a microscope or the like.

Based on such an expectation, a method of analyzing a membrane surface of an exosome by capturing a CD63-positive exosome, labeling the captured exosome with a fluorescent-modified antibody, and performing measurement through flow cytometry, using a bead modified with an antibody to CD63 expressed on the membrane surface of the exosome as an antigen, has been proposed (see Non-Patent Document 1).

PRIOR ART DOCUMENTS

Non-Patent Documents

Non-Patent Document 1: Lasser C., et al., J. Vis. Exp., (2012) vol. 59, e3037.

SUMMARY

However, the expression level of glycoprotein such as CD63 in the membrane surface of the exosome is low, and therefore, it is impossible to detect the expression of the glycoprotein in the membrane surface of the exosome in the method of analyzing an exosome disclosed in Non-Patent Document 1 unless a plurality of particles of exosomes are captured by an antibody-modified bead using many samples. There is still room for improvement in the method of analyzing an exosome disclosed in Non-Patent Document 1 in view of simply analyzing an exosome derived from the samples with high sensitivity.

An object of aspects of the present invention is to provide an exosome analysis method, an exosome analysis apparatus, an antibody-exosome complex, and an exosome electrophoresis chip with which it is possible to analyze an exosome with high sensitivity.

The present inventors have conducted extensive studies, and as a result, they have found that problems can be solved by measuring a zeta potential of a complex formed of an exosome and an antibody to a protein existing on the membrane surface of the exosome as an antigen. Embodiments of the present invention provide the following (1) to (7).

(1) A method of analyzing an exosome according to an embodiment of the present invention, including:

(a) a step of preparing an exosome from a sample;

(b) a step of bringing the exosome prepared in the step (a) into contact with a first antibody to a protein which exists on the surface of the exosome as an antigen and forming a first antibody-exosome complex; and (c) a step of measuring a zeta potential of the first antibody-exosome complex.

(2) An exosome analysis apparatus according to the embodiment of the present invention, including:

preparation means for preparing an exosome from a sample;

complex formation means for bringing the exosome into contact with an antibody to a protein which exists on the surface of the exosome as an antigen and forming an antibody-exosome complex; and measurement means for measuring a zeta potential of the antibody-exosome complex.

(3) An antibody-exosome complex according to the embodiment of the present invention, including:

an exosome prepared from a sample; and an antibody to a protein which exists on the surface of the exosome as an antigen, wherein a zeta potential of the antibody-exosome complex which is calculated using electrophoresis mobility has a positive electric charge compared to a zeta potential of the exosome.

(4) An exosome electrophoresis chip according to the embodiment of the present invention, including:

a reservoir into which a suspension containing an antibody-exosome complex that is obtained by bringing an exosome prepared from a sample into contact with an antibody to a protein which exists on the surface of the exosome as an antigen is injected; and a flow path in which electrophoresis of the suspension containing the antibody-exosome complex is performed.

(5) A method of analyzing an exosome according to the embodiment of the present invention, including:

(a) a step of preparing an exosome from a sample;

(b) a step of bringing the exosome prepared in the step (a) into contact with a molecule which specifically binds to a biomolecule existing on the surface of the exosome and forming a complex; and (c) a step of measuring a zeta potential of the complex.

(6) An exosome analysis apparatus according to the embodiment of the present invention, including:

preparation means for preparing an exosome from a sample;

complex formation means for bringing the exosome into contact with a molecule which specifically binds to a biomolecule existing on the surface of the exosome and forming a complex; and measurement means for measuring a zeta potential of the complex.

(7) An exosome electrophoresis chip according to the embodiment of the present invention, including:

a reservoir into which a suspension containing a complex that is obtained by bringing an exosome prepared from a sample into contact with a molecule which specifically binds to a biomolecule existing on the surface of the exosome is injected; and a flow path in which electrophoresis of the suspension containing the complex is performed.

According to aspects of the present invention, it is possible to analyze an exosome with high sensitivity.

DETAILED DESCRIPTION

Hereinafter, preferred examples of the present invention will be described, but the present invention is not limited to these examples. Addition, omission, replacement, and other modifications of the components can be made within the scope not departing from the gist of the present invention.

<Exosome Analysis Method>

A method of analyzing an exosome of the present embodiment is a method of analyzing an exosome for detecting abnormality in a cell, and includes:

(a) a step of preparing an exosome from a sample containing the exosome which is secreted by a cell to be detected;

(b) a step of bringing the exosome prepared in step (a) into contact with a first antibody to a protein which exists on the surface of the exosome as an antigen and forming a first antibody-exosome complex; and (c) a step of measuring a zeta potential of the first antibody-exosome complex.

The exosome is a secretion of a cell and expresses protein derived from a cell of a secretory source on its surface. An abnormal cell such as a cancer cell existing in a living body expresses unique protein in its cell membrane.

For this reason, it is possible to detect abnormality in a cell of a secretory source by analyzing the protein expressed on the surface of the exosome. Here, the surface of the exosome is a membrane surface of a membrane vesicle which is secreted from a cell and refers to a part in which the secreted exosome is brought into contact with the environment within a living body.

Furthermore, the exosome is detected in blood circulating in a living body, and therefore, it is possible to detect abnormality in the living body by analyzing the exosome without performing a biopsy.

Hereinafter, each of steps will be described.

Step (a) is a step of preparing an exosome from a sample containing the exosome secreted by a cell to be detected. The sample is a sample which can be obtained from the environment where the cell to be detected is surrounded, and the sample is not particularly limited as long as the sample contains the exosome secreted by the cell, and examples thereof include samples such as blood, urine, breast milk, bronchioalveolar lavage fluids, amniotic fluids, malignant effusions, and saliva. It is easy to detect the exosome using blood or urine. Furthermore, examples of blood include blood plasma in terms of easy detection of the exosome.

In addition, the sample also includes a cell culture liquid containing an exosome secreted by a culture cell.

Examples of the cell to be detected include cancer cells, mastocytes, dendritic cells, reticulocytes, epithelial cells, B cells, and neurons which are known to produce an exosome.

Examples of the method of preparing an exosome from the sample include methods such as ultracentrifugation, ultrafiltration, continuous flow electrophoresis, and chromatography. Examples of the ultrafiltration and chromatography include methods such as a filtration method using a size filter, or gel filtration chromatography.

Step (b) is a step of bringing the exosome prepared in step (a) into contact with a first antibody to a protein which exists on the surface of the exosome as an antigen and forming a first antibody-exosome complex.

In step (b), the contact means that, for example, protein, which exists on the surface of an exosome, and an antibody to the protein as an antigen interact with each other while causing antigen-antibody reaction.

An abnormal cell secreting an exosome expresses unique protein on the surface of the cell thereof, or expression of unique protein is deficient in the abnormal cell. Accordingly, it is possible to detect abnormality in a cell using an antibody to a protein having a different expression pattern compared to a normal cell, as an antigen.

From this point of view, for example, a first antibody to a protein which is highly expressed in an abnormal cell or a normal cell as an antigen. In addition, for example, the first antibody to a protein which is specifically expressed in an abnormal cell or in a normal cell as an antigen.

For example, protein such as CD10, CD5/6, CAV1, MOESIN, and ETS1 are highly expressed in a normal mammary gland epithelial cell strain. In contrast, it has been reported that the expression of such protein is decreased in a breast cancer cell strain (Charafe-Jauffret E, et al., Oncogene (2006) vol. 25, pp. 2273-2284). For example, when detecting abnormality in a mammary gland epithelial cell, antibodies of these are used as first antibodies.

The antigen recognized by the first antibody is not particularly limited as long as the antigen is protein existing on the surface of an exosome, and a part of protein existing in a cell may be exposed on the surface. For example, a component (hereinafter, also referred to as a cancer antigen) which is attacked by an immunocyte in a cancer cell is decomposed into a peptide in cytoplasm of the cancer cell, and is expressed as a cancer antigen peptide with a class IMHC molecule on the surface of a cell membrane of the cancer cell. The antigen recognized by the first antibody may be the cancer antigen peptide.

For example, the first antibody to a membrane protein such as a receptor as an antigen in terms of easy formation a complex with an exosome.

Accordingly, when detecting abnormality in a mammary gland epithelial cell, for example, the first antibody to a membrane protein such as CD10, CD5/6, and CD44 as an antigen.

In addition, the first antibody may be formed of a plurality of types of antibodies, and the plurality of types of antibodies may recognize different epitopes of an identical antigen. It is possible to increase recognition accuracy of an exosome having a specific antigen using the antibodies.

In addition, the plurality of types of antibodies may recognize different antigens. For example, it is possible to increase accuracy, when detecting abnormality in the mammary gland epithelial cell, using the plurality of types of antibodies to a plurality of types of protein, which are highly expressed in breast cancer cells or normal mammary gland epithelial cells, as antigens.

In addition, the first antibody is not limited to antibodies relating to cancer. It is possible to detect abnormality relating to obesity, diabetes, neurodegenerative disease, and the like in a target cell using an antibody relating to such diseases as the first antibody.

Step (c) is a step of measuring a zeta potential of the first antibody-exosome complex. The zeta potential is an index of electrification of surfaces of particles dispersed in an aqueous solution, and is strictly defined as a potential of a "sliding surface" when particles dispersed in an aqueous solution move by being applied with an electric field. The zeta potential can be obtained by applying the Smoluchowski equation or the like to mobility of particles which can be measured through an electrophoresis test. The antibody is positively charged while the exosome is negatively charged. Therefore, when the first antibody and the exosome form a complex, the zeta potential of the complex is positively shifted compared to a zeta potential of a single exosome.

Accordingly, it is possible to detect expression of protein which is recognized by the first antibody on the membrane surface of an exosome and to detect abnormality in a cell of a secretory source by measuring the zeta potential of the complex.

In addition, in the analysis method of the present embodiment, it is unnecessary to capture a large number of exosomes using a bead modified with an antibody unlike the exosome analysis method in the related art. For this reason, it is possible to simply detect abnormality in the cell with high sensitivity according to the analysis method of the present embodiment.

Furthermore, step (c) is, for example, a step of separating the first antibody-exosome complex from other substances such as free-antibodies, free-exosomes, and other samples or materials through electrophoresis and measuring a zeta potential of the first antibody-exosome complex at one particle level.

For example, when preparing exosomes from blood circulating in a living body, the exosomes are secreted from a plurality of types of cells derived from a plurality of organs. Therefore, the type and the expression level of protein existing on the membrane surfaces of the exosome vary depending on the particles. Accordingly, in order to analyze the exosome in detail, for example, the exosome is analyzed by separating the first antibody-exosome complex from other substances such as free-antibodies, free-exosomes, and other samples or materials through electrophoresis at one particle level. As the number of molecules of an antibody which bind to the exosome in one particle is larger, the complex is positively charged and the moving speed of the complex in electrophoresis becomes slower.

Furthermore, step (c) includes, for example, a step of measuring the zeta potential of the first antibody-exosome complex based on the mobility which is optically measured. Step (c) includes, for example, a step of measuring the zeta potential of the first antibody-exosome complex based on the mobility which is measured by obtaining a particle image using scattered light.

For example, during electrophoresis, the electrophoresis mobility of an antibody-exosome complex is measured by irradiating the antibody-exosome complex with a laser beam with, for example, a wavelength of 488 nm and an intensity of 50 mW and obtaining a particle image using Rayleigh scattered light. It is possible to analyze the exosome in a sample at one particle level by separating a plurality of types of antibody-exosome complexes from other substances such as free-antibodies, free-exosomes, and other samples or materials through electrophoresis and calculating the zeta potential from the electrophoresis mobility of the complex using the Smoluchowski equation.

Zeta potential (ζ)=electrophoresis mobility (u)×viscosity of solution (η)/relative permittivity of solution ($\epsilon_r$)/permittivity in vacuum ($\epsilon_0$) [Equation 1]

It is considered that since a cancer stem cell is a cell which becomes a foundation of tumor tissue formation and resistance to treatment is high, the cancer stem cell becomes an origin of recurrence and metastasis of cancer. For example, cancer can recur if a small number of cancer stem cells survive even if the majority of cancer cells are removed through treatment, and it is considered that this is a reason that recurrence of cancer can frequently occur. Accordingly, it is expected that if it is possible to remove the cancer stem cell as a target, this will lead to development of treatment which is effective also in prevention of metastasis or recurrence of cancer.

It has been reported that, in solid cancer such as breast cancer, pancreatic cancer, stomach cancer, and colorectal cancer, CD44-positive cancer cells have high tumorigenic potential in an immunodeficient mouse and have characteristics like cancer stem cells.

Therefore, according to the present embodiment, it is possible to detect a small number of metastatic breast cancer cells or the like which highly express CD44 by preparing an exosome from blood circulating in a living body; using an antibody to CD44 as an antigen, as a first antibody; separating an anti-CD44 antibody-exosome complex from other substances such as free-CD44 antibodies, free-exosomes, and other samples or materials through electrophoresis; and measuring a zeta potential of the anti-CD44 antibody-exosome complex at one particle level.

The method of analyzing an exosome of the present embodiment further includes, for example:

(d) a step of bringing the exosome prepared in step (a) into contact with a second antibody to a protein which exists on the membrane surface of the exosome as an antigen and forming a second antibody-exosome complex; and (e) a step of measuring a zeta potential of the second antibody-exosome complex, after step (c).

That is, for example, the method of analyzing an exosome of the present embodiment has a step of measuring the zeta potential of the complex with the exosome using the second antibody which is different from the first antibody, in addition to step of measuring the zeta potential of the complex with the exosome using the above-described first antibody.

Hereinafter, each step will be described in detail.

Step (d) is a step of bringing the exosome prepared in step (a) into contact with a second antibody to a protein which exists on the membrane surface of the exosome as an antigen and forming the second antibody-exosome complex;

The second antibody is, for example, different from the first antibody, and can specify characteristics different from those of a detected cell specified using the first antibody. For example, when an antibody to a protein which is specifically expressed in cancer as an antigen, is used as the first antibody, an antibody to a protein which is specifically expressed in an organ as an antigen, is used as the second antibody. Accordingly, it is possible to specify from which organ in a living body a cell of a secretory source of an exosome is derived as well as to specify whether the cell of the secretory source of the exosome is a cancer cell.

For example, examples of the protein which is specifically expressed in an organ include prostate cancer markers such as PSA, PSCA, and PSMA; and breast cancer markers such as CA15-3, BCA225, and HER2. It is possible to specify carcinoma of a cancer cell to be detected, using antibodies to these as antigens, as the second antibody.

Step (e) is a step of measuring the zeta potential of the second antibody-exosome complex. The step is the same as step (c) except for using the second antibody-exosome complex instead of the first antibody-exosome complex.

Step (e) is also a step of, for example, separating the second antibody-exosome complex from other substances such as free-antibodies, free-exosomes, and other samples or materials through electrophoresis and measuring the zeta potential of the second antibody-exosome complex at one particle level in terms of analyzing the exosome in detail.

In addition, step (e) includes, for example, a step of measuring the zeta potential of the second antibody-exosome complex based on mobility which is optically measured. Step (e) includes, for example, a step of measuring the zeta potential of the second antibody-exosome complex based on the mobility which is measured by obtaining a particle image using scattered light.

A method of analyzing an exosome of the present embodiment is an exosome analysis method for detecting abnormality in a cell, and includes:

(a) a step of preparing an exosome from a sample;

(b) a step of bringing the exosome prepared in step (a) into contact with a molecule which specifically binds to a biomolecule existing on the surface of the exosome and forming a complex; and (c) a step of measuring a zeta potential of the complex.

For example, step (c) is a step of separating the complex from other substances such as free-antibodies, free-exosomes, and other samples or materials through electrophoresis and measuring the zeta potential of the complex at one particle level.

<Exosome Analysis Apparatus>

An exosome analysis apparatus of the present embodiment is an exosome analysis apparatus for detecting abnormality in a cell, and includes:

preparation means for preparing an exosome from a sample containing the exosome which is secreted by a cell to be detected;

complex formation means for bringing the exosome into contact with an antibody to a protein which exists on the surface of the exosome as an antigen and forming an antibody-exosome complex; and measurement means for measuring a zeta potential of the antibody-exosome complex.

For example, the exosome analysis apparatus further includes electrophoresis means for separating the antibody-exosome complex from other substances such as free-antibodies, free-exosomes, and other samples or materials through electrophoresis.

In recent years, development in micro-total analysis systems (μ-TAS) aiming for high speed, high efficiency, and integration of a test, or microminiaturization of an examination device in an extracorporeal diagnostic field has been in progress.

The μ-TAS means a micro-fluid device which analyzes a biomolecule on one chip by providing a minute flow path, reaction chamber, and mixing chamber on the chip using a micro electro mechanical systems (MEMS) technique. The μ-TAS is superior to the examination device in the related art in that the μ-TAS can perform measurement and analysis with a small number of samples, is portable, and is disposable at low cost.

Furthermore, the μ-TAS has attracted attention as a highly useful method in a case of using expensive reagent or in a case of examining many specimens with small amounts.

Accordingly, in order to analyze a small number of exosomes secreted by a cell to be detected, the micro-fluid device is provided in, for example, at least a portion of the exosome analysis apparatus of the present embodiment.

Hereinafter, an example of the exosome analysis apparatus of the present embodiment will be described with reference to FIG. 1.

Figure 1:
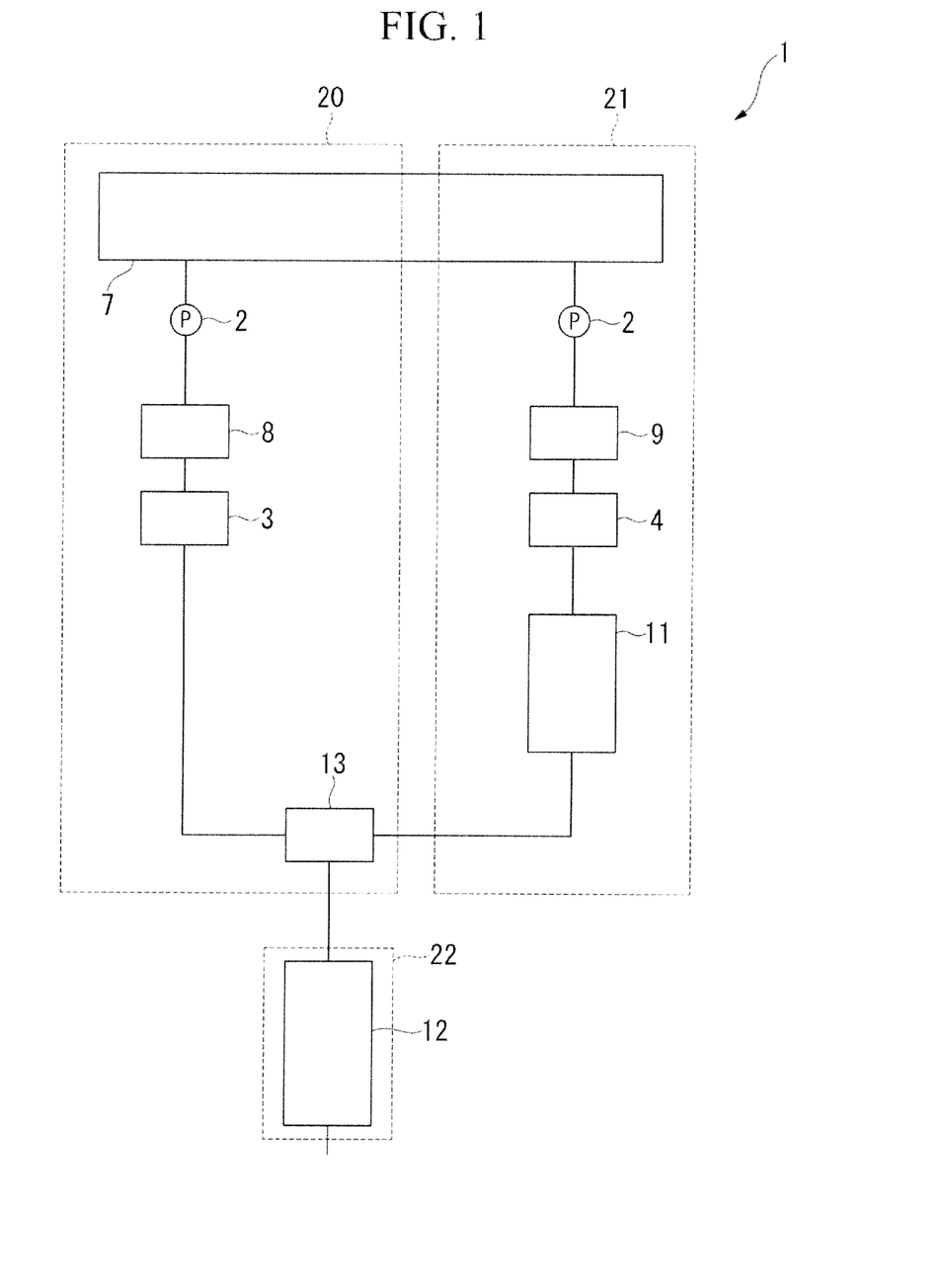
FIG. 1 is a schematic view of a mode of an exosome analysis apparatus in one embodiment.

FIG. 1 is a schematic view showing a basic configuration of an exosome analysis apparatus 1 of the present embodiment. The exosome analysis apparatus 1 of the present embodiment is used as an apparatus for preparing an exosome from a blood specimen and for detecting abnormality in a cell of a secretory source through analysis of the exosome.

The exosome analysis apparatus 1 of the present embodiment is configured to have preparation means (preparation portion) 21 configured to have liquid reservoir portions 4 and 7, a driving source 2, a valve 9, and a purification device 11; complex formation means (complex formation portion) 20 configured to have liquid reservoir portions 3 and 7, driving source 2, a valve 8, and a confluence portion 13; and measurement means (measurement portion) 22 configured to have an electrophoresis tank 12.

As shown in FIG. 1, the exosome analysis apparatus 1 of the present embodiment has the liquid reservoir portions 3 and 4 in the downstream of the driving source 2, and an antibody and blood are respectively stored in the liquid reservoir portions 3. A driving liquid is stored in the liquid reservoir portion 7 positioned upstream of the driving source 2. Furthermore, valves 8 and 9 which control the flow of a fluid are provided in the flow path of the upstream of the liquid reservoir portions 3 and 4.

First, the valve 9 is opened and a blood specimen which is stored in the liquid reservoir portion 4 is pushed by the driving source 2, and the pushed blood specimen passes through the purification device 11. The purification device 11 is constituted of a filter portion for sorting only blood plasma from blood; and a gel filtration column for sorting components in the blood plasma in size. An exosome fraction which has passed through the purification device 11 is stored in the confluence portion 13 with a valve in a closed state.

Next, the valve 8 is opened and an antibody which is stored in the liquid reservoir portion 3 is pushed by the driving source 2, and the exosome is brought into contact with the antibody in the confluence portion 13 and antibody-exosome is formed.

Next, the valve attached to the confluence portion 13 is opened and the antibody-exosome passes through the electrophoresis tank 12. The electrophoresis tank 12 is connected to an electrophoresis device which is not shown in the drawing, and a zeta potential of the antibody-exosome complex is measured by the electrophoresis device.

In this manner, it is possible to simply analyze a minute number of exosomes in a living body with high sensitivity according to the exosome analysis apparatus 1 of the present embodiment.

An exosome analysis apparatus of the present embodiment is an exosome analysis apparatus for detecting abnormality in a cell, and includes:

preparation means for preparing an exosome from a sample;

complex formation means for bringing the exosome into contact with a molecule which specifically binds to a biomolecule existing on the surface of the exosome and forming a complex; and measurement means for measuring a zeta potential of the complex.

For example, the exosome analysis apparatus further includes electrophoresis means for separating the complex from other substances such as free-antibodies, free-exosomes, and other samples or materials through electrophoresis.

<Antibody-exosome Complex>

An antibody-exosome complex according to the embodiment is an antibody-exosome complex for detecting abnormality in a cell, and includes:

an exosome prepared from a sample; and an antibody to a protein which exists on the surface of the exosome as an antigen, wherein a zeta potential of the antibody-exosome complex which is calculated using electrophoresis mobility has a positive electric charge compared to a zeta potential of the exosome.

In addition, the antibody-exosome complex of the present embodiment can be used in, for example, measuring of the zeta potential as described above.

Furthermore, in the physical property of the antibody-exosome complex of the present embodiment, the zeta potential of the antibody-exosome complex is shifted by, for example, 0.1 mV or greater or 1 mV or greater compared to that of the single exosome. In addition, the zeta potential of the antibody-exosome complex is shifted by, for example, 0.5 mV, 1 mV, 2 mV, 3 mV, 4 mV, or 5 mV or greater compared to the zeta potential of the single exosome.

The antibody-exosome complex of the present embodiment is the same as that in the method of analyzing an exosome of the present embodiment described above, and therefore, the description thereof will not be repeated.

<Exosome Electrophoresis Chip>

An exosome electrophoresis chip of the present embodiment is an exosome electrophoresis chip for detecting abnormality in a cell, and includes:

a reservoir into which a suspension containing an antibody-exosome complex that is obtained by bringing an exosome prepared from a sample into contact with an antibody to a protein which exists on the surface of the exosome as an antigen is injected; and a flow path in which electrophoresis of the suspension containing the antibody-exosome complex is performed.

The exosome electrophoresis chip further includes, for example, two portions into which an electrode for applying a voltage to the flow path can be introduced. The two portions are respectively provided at arbitrary positions within two reservoirs one by one. In addition, the exosome electrophoresis chip further includes, for example, an electrode for applying the voltage to the flow path.

The flow path has, for example, a portion which is irradiated with light in order to calculate a zeta potential of the antibody-exosome complex. In addition, for example, at least one portion of the flow path is coated with a polymer in order to suppress non-specific adsorption of a biomolecule. Examples of the polymer include a polymer used in blocking the adsorption of protein such as polyethylene glycol (PEG) or bovine serum albumin (BSA), and 2-methacryloyloxyethylphosphorylcholine (MPC) is particularly preferable in view of suppressing the non-specific adsorption of protein.

An exosome electrophoresis chip of the present embodiment is an exosome electrophoresis chip for detecting abnormality in a cell, and includes:

a reservoir into which a suspension containing a complex that is obtained by bringing an exosome prepared from a sample into contact with a molecule which specifically binds to a biomolecule existing on the surface of the exosome is injected; and a flow path in which electrophoresis of the suspension containing the complex is performed.

Hereinafter, the present invention will be described using Examples, but the present invention is not limited to the Examples.

EXAMPLES

Example 1

[Preparation of Exosome Suspension]

Human mammary gland epithelial cells MCF10A were cultured until they reached confluence using a mammary gland epithelial cell culture kit (manufactured by Lonza Group, Ltd.). In addition, human breast cancer cells MDA-MB-231 were cultured until they reached confluence using an RPMI culture medium (manufactured by Invitrogen Corporation) containing 10% fetal bovine serum (manufactured by Invitrogen Corporation), 100 units/mL of penicillin (manufactured by Invitrogen Corporation), 100 µg/mL of streptomycin (manufactured by Invitrogen Corporation), and 100 µg/mL of kanamycin (manufactured by Invitrogen Corporation).

Next, the culture medium was exchanged, and MCF10A and MDA-MB-231 were cultured in a serum-free culture medium (RPMI culture medium (manufactured by Invitrogen Corporation) containing 100 units/mL of penicillin (manufactured by Invitrogen Corporation), 100 µg/mL of streptomycin (manufactured by Invitrogen Corporation), and 100 µg/mL of kanamycin (manufactured by Invitrogen Corporation)) for one day, to collect culture supernatant.

Supernatant was collected by centrifuging the culture supernatant at 2000×g for 15 minutes, supernatant was collected by centrifuging the collected supernatant at 16800×g for 35 minutes, and the further collected supernatant was centrifuged at 151000×g for 70 minutes. The supernatant was discarded, the sediment was suspended in PBS, and the suspension was centrifuged at 151000×g for 70 minutes. Furthermore, supernatant was discarded and the sediment was suspended in PBS to obtain an exosome suspension.

[Formation of Antibody-exosome Complex]

An antibody-exosome suspension, which was obtained by adding an anti-human CD10 antibody (manufactured by Becton, Dickinson and Company, product code: 555746) suspension or a Mouse IgG1, κ isotype control antibody (manufactured by Becton, Dickinson and Company, product code: 349050) suspension to each of the exosome suspensions which were prepared from the culture supernatants of MCF10A and MDA-MB-231, was stirred and reacted at 4° C. for 30 minutes to attempt to form an antibody-exosome complex.

[Measurement of Zeta Potential of Antibody-exosome Complex]

750 μL of an antibody-exosome suspension was put into a sample cell, and a zeta potential was measured using a zeta potential measurement device (manufactured by Malvern Instruments Ltd., trade name: Zetasizer Nano) under conditions of 25° C. and 20V. The test was continuously performed three times. The measurement results were shown in FIG. 2.

Figure 2:
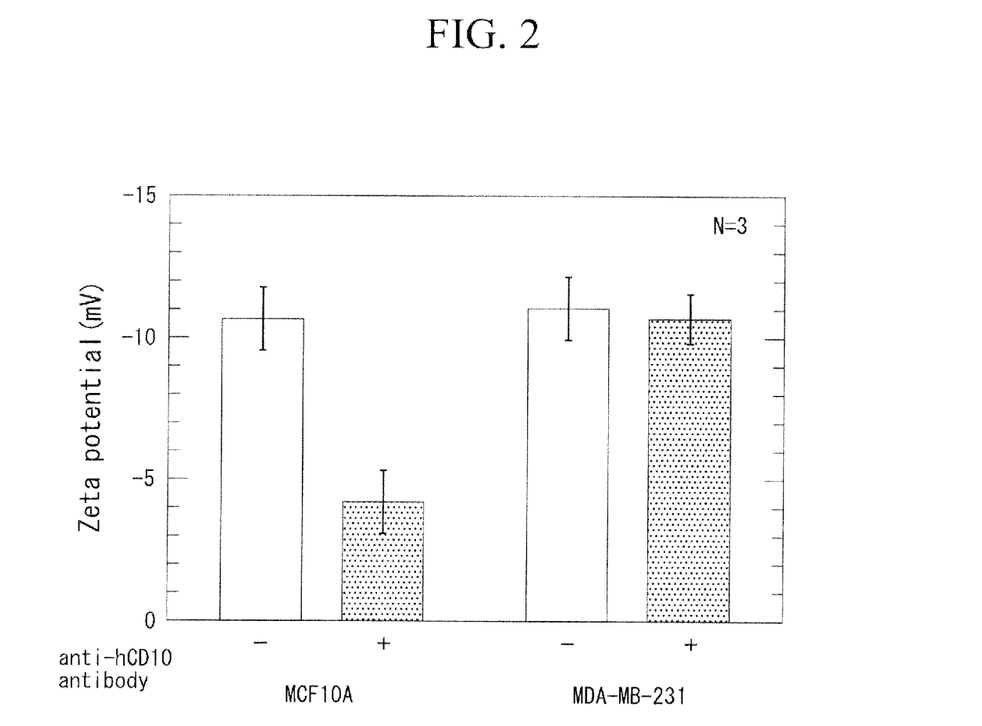
FIG. 2 is a measurement result of a zeta potential of an antibody-exosome complex in Example 1.

As shown in FIG. 2, in MCF10A, it was confirmed that the zeta potential of the anti-human CD10 antibody-exosome suspension was more increased compared to the Mouse IgG1, κ isotype control antibody-exosome suspension.

For this reason, it was found that an anti-human CD10 antibody-exosome complex was formed in the anti-human CD10 antibody-exosome suspension while no Mouse IgG1, κ isotype control antibody-exosome complex was formed in the Mouse IgG1, κ isotype control antibody-exosome suspension.

In contrast, in MDA-MB-231, it was confirmed that there was no difference in the zeta potential between the Mouse IgG1, κ isotype control antibody-exosome suspension and the anti-human CD10 antibody-exosome suspension, and therefore, no complex was formed in either suspension.

It has been reported that CD10 is highly expressed in MCF10A which are normal cells and is not expressed in MDA-MB-231 which are cancer cells (Charafe-Jauffret E, et al., Oncogene (2006) vol. 25, pp. 2273-2284).

According to Example 1, it is possible to confirm existence of a cell which is a secretory source of an exosome by measuring the zeta potential of the antibody-exosome complex utilizing an antibody to a protein, of which the expression level is high in a certain cell, as an antigen. That is, it is clear that it is possible to detect abnormality of a cell of a secretory source of an exosome and to simply detect cancer existing in a living body with high sensitivity, by measuring the zeta potential of the antibody-exosome suspension utilizing an antibody to a protein which is specifically expressed in a cancer cell, or protein which is highly expressed in a cancer cell as an antigen.

Example 2

[Preparation of Exosome Suspension]

An exosome suspension derived from human breast cancer cells MDA-MB-231 was prepared through the same method in Example 1.

[Formation of Antibody-exosome Complex]

An antibody-exosome suspension, which was obtained by adding an anti-human CD63 antibody (manufactured by Becton, Dickinson and Company, product code: 556019) suspension or a Mouse IgG2a isotype control antibody (manufactured by Becton, Dickinson and Company, product code: 555746) suspension to each of the exosome suspension which were prepared from the each culture supernatant of MDA-MB-231, was stirred and reacted at 4° C. for 30 minutes to attempt to form an antibody-exosome complex. In addition, an exosome suspension which was not added with an antibody suspension was prepared as a negative control under the same conditions.

[Measurement of Zeta Potential of Antibody-exosome Complex Using Electrophoresis Chip]

Figure 3:
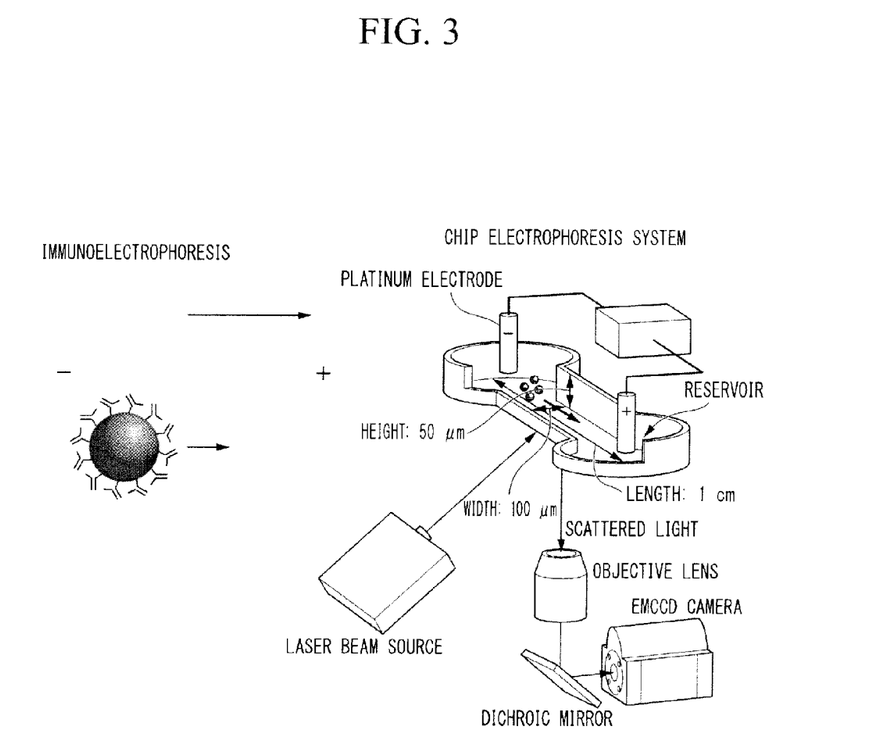
FIG. 3 is a schematic view showing a step of measuring a zeta potential of an antibody-exosome complex using microcapillary electrophoresis in Example 2.

Electrophoresis of the antibody-exosome suspension was performed using a chip electrophoresis system shown on the right side in FIG. 3, and a zeta potential of an antibody-exosome complex was measured. The details are shown below.

(Manufacturing Polydimethylsiloxane (PDMS) Electrophoresis Chip)

A PDMS electrophoresis chip was manufactured through a soft lithography method. The size of a flow path in the electrophoresis chip is 200 μm wide, 50 μm tall, and 1000 μm long. The inner wall of the flow path was coated with a 2-methacryloyloxyethylphosphorylcholine (MPC) polymer in order to suppress non-specific adsorption of protein.

(Microcapillary Electrophoresis Using Antibody-Exosome Complex)

An antibody-exosome suspension was added to one of reservoirs provided on both sides of the manufactured PDMS electrophoresis chip and was sucked by a syringe from the other side, and an exosome suspension or an antibody-exosome suspension was introduced into the flow path in the electrophoresis chip. A platinum electrode was introduced to both the reservoirs and a voltage was applied at an electric field intensity of 50 V/cm for 10 seconds to perform electrophoresis.

The left side in FIG. 3 is an enlarged view of electrophoresis of each of the exosome and the antibody-exosome complex. The antibody is positively charged while the exosome is negatively charged, and therefore, a zeta potential of the antibody-exosome complex has a positive electric charge compared to a zeta potential of the single exosome. Accordingly, the mobility of the antibody-exosome complex becomes smaller than the mobility of the exosome.

Furthermore, the electrophoresis chip was irradiated with a laser beam with a wavelength of 488 nm and an intensity of 50 mW from the lower side direction, and exosome-derived scattered light which is emitted light was condensed with an object lens (magnification ×60) on the lower side of the electrophoresis chip.

Next, images of the exosome and the antibody-exosome complex were acquired using high-sensitivity camera EMCCD iXon3 manufactured by Andor Co., Ltd., and the electrophoresis mobility was calculated by dividing the moving speed of each of the exosome and the antibody-exosome complex by the electric field intensity. In addition, the electrophoresis mobility of a non-charged bead was measured to calculate the electrophoresis mobility of an electroosmotic flow in the flow path. Moreover, the electrophoresis mobility of the non-charged bead was subtracted from the electrophoresis mobility of each of the exosome and the antibody-exosome complex to calculate the true electrophoresis mobility of each of the exosome and the antibody-exosome complex.

Next, a zeta potential was calculated from the true electrophoresis mobility of each of the exosome and the antibody-exosome complex using Smoluchowski equation.

The results are shown in FIG. 3 and Table 1.

TABLE 1

|  | (−) anti-CD63 | (+) anti-CD63 | Isotype control |
|---|---|---|---|
| Zeta potential (mV) | −9.94 ± 2.44 | −2.88 ± 3.87 | −7.52 ± 1.48 |

Figure 4:
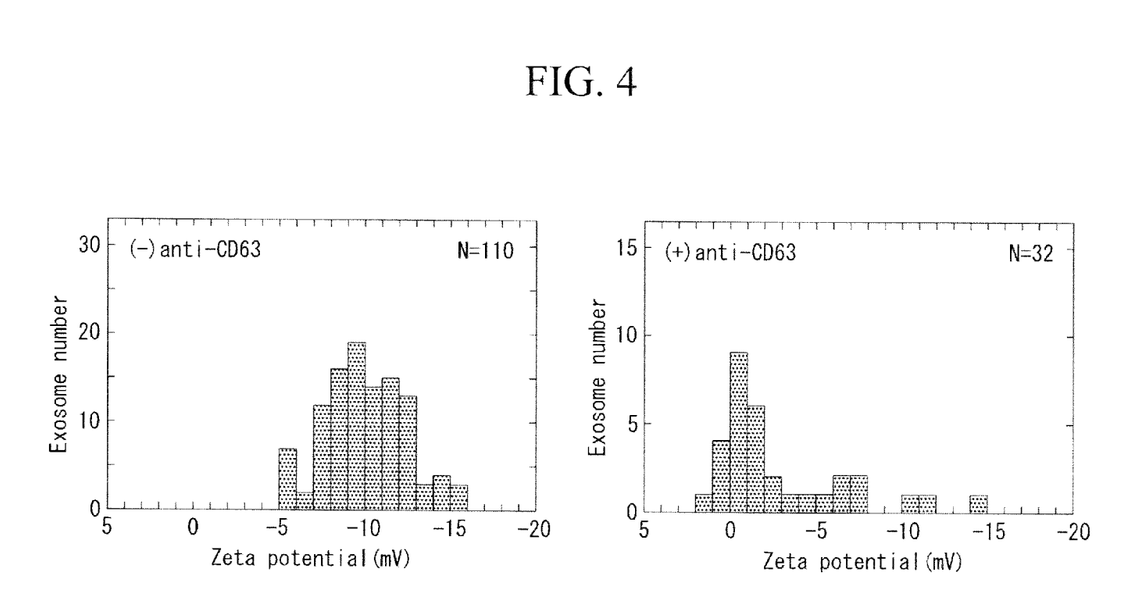
FIG. 4 is a measurement result of the zeta potential of the antibody-exosome complex using the microcapillary electrophoresis in Example 2.

The left side in FIG. 4 shows distribution of zeta potentials in the exosome suspension. The horizontal axis shows the zeta potential and the longitudinal axis shows the number of exosomes. The zeta potentials of total 110 exosomes were measured. As shown in Table 1, the average value of the zeta potentials in the exosome suspension was −9.94 mV±2.44 mV. In addition, the average value of the zeta potentials in the Mouse IgG2a control antibody-exosome suspension was −7.52 mV±1.48 mV, and showed a value approximate to the average value of the zeta potential in the exosome suspension.

The right side in FIG. 4 shows distribution of zeta potentials in the anti-human CD63 antibody-exosome suspension. The horizontal axis shows the zeta potential and the longitudinal axis shows the number of exosomes. The zeta potentials of total 32 exosomes were measured. As shown in Table 1, the average value of the zeta potentials in the anti-human CD63 antibody-exosome suspension was −2.88 mV±3.87 mV. In addition, it was confirmed that the zeta potential of an anti-human CD63 antibody-exosome suspension was more increased compared to the exosome suspension and the Mouse IgG2a control antibody-exosome suspension.

For this reason, it was found that an anti-human CD63 antibody-exosome complex was formed in the anti-human CD63 antibody-exosome suspension while no Mouse IgG2a isotype control antibody-exosome complex was formed in the Mouse IgG2a isotype control antibody-exosome suspension.

As shown on the right side in FIG. 4, it is possible to measure the zeta potential of the antibody-exosome complex at one particle level as well as the average value of the zeta potentials of the antibody-exosome complex using the electrophoresis chip. For this reason, even when it is considered that there is no exosome, which has an antigen recognized by an antibody, in a sample from the average value of the zeta potentials, it is possible to detect an exosome, which has the antigen existing as a minor population, using the electrophoresis chip.

That is, according to Example 2, it is clear that it is possible to, for example, detect cancer cells with a high degree of malignancy in a living body in very small numbers with high sensitivity, and to early detect any invasion and metastasis of cancer.

Furthermore, from the results of Example 1 and Example 2, for example, it is possible to specify from which organ a cancer cell to be detected is derived by first measuring the zeta potential of the first antibody-exosome complex utilizing an antibody to a protein which is specifically expressed in a cancer cell as an antigen as a first antibody, and next measuring the zeta potential of the second antibody-exosome complex utilizing an antibody to a protein which is specifically expressed in an organ as an antigen as a second antibody. In addition, it is possible to specify abnormality of a cell in a living body in detail by changing the combination of the antibody used, without being limited to the cancer cell.

From the above-described results, it is clear that it is possible to simply analyze an exosome with high sensitivity in detail according to the present embodiment.

INDUSTRIAL APPLICABILITY

Embodiments of the present invention can provide an exosome analysis method and an exosome analysis apparatus with which it is possible to simply analyze an exosome with high sensitivity.

What is claimed is:
1. A method of analyzing an exosome, comprising:
   (a) preparing an exosome from a sample;
   (b) bringing the exosome prepared in (a) into contact with a first antibody to a protein that exists on the surface of the exosome as an antigen thereby forming a first antibody-exosome complex;
   (c) irradiating the first antibody-exosome complex with a laser beam to obtain a particle image of the first antibody-exosome complex using scattered light, while separating the first antibody-exosome complex from other substances through electrophoresis;
   (d) determining an electrophoresis mobility of the first antibody-exosome complex based on the particle image; and
   (e) determining a zeta potential of the first antibody-exosome complex based on the electrophoresis mobility of the first antibody-exosome complex.

2. The method of analyzing an exosome according to claim 1, wherein the protein is highly expressed in an abnormal cell or a normal cell.

3. The method of analyzing an exosome according to claim 1, wherein the protein is specifically expressed in an abnormal cell or in a normal cell.

4. The method of analyzing an exosome according to claim 1, wherein the first antibody is formed of a plurality of types of antibodies.

5. A method of analyzing an exosome comprising;
   (a) preparing an exosome from a sample;
   (b) bringing the exosome prepared in (a) into contact with a first antibody to a protein that exists on the surface of the exosome as an antigen and forming a first antibody-exosome complex;
   (c) measuring a zeta potential of the first antibody-exosome complex (d) bringing the exosome prepared in (a) into contact with a second antibody to a protein that exists on the surface of the exosome as an antigen and forming a second antibody-exosome complex; and
   (e) measuring a zeta potential of the second antibody-exosome complex, after (c).

6. The method of analyzing an exosome according to claim 5, wherein (e) comprises separating the second antibody-exosome complex from other substances through electrophoresis and measuring the zeta potential of the second antibody-exosome complex at one particle level.

7. The method of analyzing an exosome according to claim 6, wherein (e) comprises measuring the zeta potential of the second antibody-exosome complex based on mobility which is optically measured.

8. The method of analyzing an exosome according to claim 6, wherein (e) comprises measuring the zeta potential of the second antibody-exosome complex based on mobility which is measured by obtaining a particle image using scattered light.

9. The method of analyzing an exosome according to claim 5, wherein the protein is highly and specifically expressed in an organ as an antigen.

10. An exosome analysis apparatus, comprising:
   a preparation member configured for preparing an exosome from a sample;
   a complex formation member configured for bringing the exosome into contact with an antibody to a protein that exists on the surface of the exosome as an antigen and thereby forming an antibody-exosome complex;
   an electrophoresis member configured for separating the antibody-exosome complex from other substances through electrophoresis;
   a laser beam source for irradiating the antibody-exosome complex;
   a high-sensitivity camera for obtaining a particle image of the antibody-exosome complex using scattered light to determine the electrophoresis mobility of the first antibody-exosome complex; and a zeta potential measuring member for measuring zeta potential based on the electrophoresis mobility of the first antibody-exosome complex.

11. A method of analyzing an exosome, comprising:
(a) preparing an exosome from a sample;
(b) bringing the exosome prepared in (a) into contact with a molecule that specifically binds to a biomolecule existing on the surface of the exosome thereby forming a complex;
(c) irradiating the complex with a laser beam to obtain a particle image of the complex using scattered light, while separating the complex from other substances through electrophoresis;
(d) determining an electrophoresis mobility of the complex based on the particle image; and
(e) determining a zeta potential of the complex based on the electrophoresis mobility of the first antibody-exosome complex.

12. An exosome analysis apparatus, comprising:

a preparation member configured for preparing an exosome from a sample;

a complex formation member configured for bringing the exosome into contact with a molecule that specifically binds to a biomolecule existing on the surface of the exosome to form a complex;

an electrophoresis member configured for separating the complex from other substances through electrophoresis;

a laser beam source for irradiating the complex;

a high-sensitivity camera for obtaining a particle image of the complex using scattered light to determine the electrophoresis mobility of the complex; and a zeta potential measuring member for measuring zeta potential based on the electrophoresis mobility of the complex.

* * * * *